United States Patent [19]

Agreda et al.

[11] Patent Number: 4,976,947
[45] Date of Patent: Dec. 11, 1990

[54] PROCESS FOR THE RECOVERY OF ELEMENTAL IODINE FROM ALKYL IODIDES

[75] Inventors: Victor H. Agreda; Guy R. Steinmetz, both of Kingsport, Tenn.

[73] Assignee: Eastman Kodak Company, Rochester, N.Y.

[21] Appl. No.: 481,530

[22] Filed: Feb. 20, 1990

[51] Int. Cl.$^5$ .......................... C01B 7/14; C01B 7/13; C07B 53/08
[52] U.S. Cl. .................................. 423/502; 423/481; 423/507; 562/607
[58] Field of Search ............... 423/481, 488, 502, 507; 562/607, 497, 520, 406

[56] References Cited

U.S. PATENT DOCUMENTS 4,649,216 3/1987 Rule et al. ........................ 562/406
4,705,890 11/1987 Steinmetz et al. ................. 562/406
4,778,918 10/1988 Steinmetz et al. ................. 560/100

FOREIGN PATENT DOCUMENTS 132391 1/1985 European Pat. Off. ............ 423/481
1103305 2/1959 Fed. Rep. of Germany ...... 423/502

Primary Examiner—Jeffrey E. Russel
Assistant Examiner—Brian M. Bolam
Attorney, Agent, or Firm—J. Frederick Thomsen; William P. Heath, Jr.

[57] ABSTRACT

Disclosed is a process for the recovery of the iodine and alkyl value of an alkyl iodide by a process comprising (I) carbonylating an alkyl iodide by a process presence of a carbonylation catalyst, carbon monoxide and a hydrogen donor to obtain a mixture of hydrogen iodide and an acyl compound and (II) oxidizing the hydrogen iodide of step (I) to elemental iodine.

1 Claim, No Drawings

PROCESS FOR THE RECOVERY OF ELEMENTAL IODINE FROM ALKYL IODIDES

This invention pertains to a novel process for the recovery of elemental iodine from alkyl iodides. More particularly, this invention pertains to a process for the conversion of alkyl iodides to elemental iodine and acyl compounds.

The oxyiodination of various aromatic compounds in the presence of oxygen and iodine to obtain aromatic mono. and/or poly-iodides has been disclosed in the literature such as U.S. Pat. Nos. 4,795,737, 4,792,642, 4,792,641, 4,778,940, 4,778,939, 4,778,938, and 4,746,758. In many processes wherein the objective is to iodinate an aromatic compound to produce a specific aromatic iodide, undesired isomers and/or polyiodo compounds are produced as by-products. For example, in the preparation of 2,6-diiodonaphthalene, a compound useful in the manufacture of 2,6-naphthalenedicarboxylic acid and esters thereof, by the oxyiodination processes described in the above-cited patents, monoiodonaphthalenes, undesired diodonaphthalene isomers and triiodonaphthalenes also are produced. The recovery of the iodine values and recycle of the aromatic reactant in a useful form is desirable, if not essential, for both economic and environmental reasons.

The conversion of such undesired aromatic iodides to aromatic compounds and alkyl iodides may be achieved by means of a dehydrohalogenation process wherein a reactant comprising one or more aromatic iodides, including mono- and poly-iodo aromatic compounds, is contacted with hydrogen in the presence of a Group VIII metal catalyst and a compound capable of forming an alkyl halide in conjunction with the dehydrohalogenation reaction under dehydrohalogenation conditions of temperature and pressure. The process not only results in the dehydrohalogenation of aromatic halides in high yields and at excellent rates of conversion but also produces an alkyl halide. The alkyl iodide is relatively volatile and thus can be recovered simply by flashing it from the dehydrohalogenation product mixture. In addition to permitting the recovery of halogen values at reasonable cost, the process also is advantageous in that it requires lower temperatures to produce results equivalent to those accomplished through the use of known methods. The use of lower temperatures in turn reduces the extent of side-reactions such as coupling of the aromatic compounds.

Alkyl iodides also are produced when aromatic iodides are converted to aromatic carboxylic acids and/or esters by the carbonylation processes described in U.S. Pat. Nos. 4,847,406, 4,827,018, 4,803,296, 4,780,563, 4,778,918 and 4,705,890 and Published Application WO 88/05036. These carbonylation processes comprise contacting an aromatic iodide such as 2,6-diiodonaphthalene with carbon monoxide at elevated pressure and temperature in the presence of a Group VIII metal catalyst and an alkanol such as methanol.

In both the dehydrohalogenation and carbonylation processes referred to above, a volatile alkyl iodide is produced that can be easily separated in high yield from the reaction mixture. The iodine values of alkyl iodides may be recovered by the catalytic combustion process described in Published PCT Application WO 89/00986. However, this process incinerates the alkyl moiety, resulting in the loss of the value of the organic portion of the alkyl iodide. Although the alkyl iodide could be fed directly to the oxyiodination reactor, the generation of large amounts of carbon dioxide would dilute the oxygen level in the reactor. U.S. Pat. No. 4,863,710 discloses an oxidative hydrolysis of alkyl iodides to an alkanol and iodine. However, this process generates a low value organic and requires a large excess of water to force the equilibrium towards the formation of hydrogen iodide. The subsequent distillation of excess water from the hydrogen iodide/water azeotrope is a very energy intensive operation.

This invention provides a means for the economical recovery of both the iodine and organic moieties of alkyl iodides in the form of elemental iodine and high value organic compounds. We have found that both the iodine and organic values of alkyl iodides can be readily recovered in an economical manner in high yields by the carbonylation of an alkyl iodide to an acyl-containing compound and hydrogen iodide, followed by the oxidation of the hydrogen iodide to iodine. Our invention thus provides a process for the conversion of alkyl iodides to elemental iodine and an acyl compound comprising the steps of:

I. carbonylating an alkyl iodide in the presence of a carbonylation catalyst, carbon monoxide and a hydrogen donor to obtain a mixture of hydrogen iodide and an acyl compound; and II. oxidizing the hydrogen iodide of step I to elemental iodine.

The hydrogen iodide can be removed from the carbonylation mixture and oxidized by molecular oxygen to iodine, or the carbonylation reaction product can be contacted directly with molecular oxygen to convert hydrogen iodide to elemental iodine. The iodine then can be recovered and recycled to the oxyiodination reaction.

The catalytic carbonylation processes and reaction conditions for the conversion of alkyl iodides to acyl products and hydrogen iodide by a number of Group VIII metals are known. For example, J. Falbe (ed.) *New Syntheses with Carbon Monoxide, (Reactivity and Structure Concepts in Organic Chemistry;* Vol. 11) Springer-Verlag, Berlin (1980), and S. W. Polichnowski in J. Chem. Ed. 63(3) (1986) 206, the disclosure of which is incorporated herein by reference in its entirety, disclose a number of such processes. The first step of the process of the present invention includes all carbonylation processes that generate hydrogen iodide as a product. The conversion of alkyl iodides to hydrogen iodide and a number of useful and high valued acyl-containing compounds is especially useful since the acyl co-product can be varied by the use of the appropriate hydrogen donor to provide the acyl compound possessing the highest value at any particular time. For example, alkyl iodides are readily carbonylated in the presence of water to provide a carboxylic acid whereas other products such as carboxylic esters, acids and anhydrides may be obtained by performing the carbonylation in the presence of an alkanol. This versatility is not present in most processes and is an advantage of our process. Another advantage of our invention is that plant energy requirements can be reduced appreciably by controlling carefully the amount of water used to minimize the distillation of excess water from the hydrogen iodide/water azeotrope.

The oxidation of iodide to iodine by a number of oxidants is well known and can be found in any standard electrode potential table. The iodine formed in accordance with our process can be isolated by a number of procedures such as crystallization, filtration, extraction with an organic co-solvent, or decantation when the iodine is molten. The acyl values can be removed from the reaction mixture by distillation.

The alkyl iodides which may be employed by the process provided by this invention may contain from 1 to about 20 carbon atoms, and include primary, secondary, and tertiary alkyl iodides, and may contain heteroatoms such as oxygen. Preferably, the alkyl iodide is a primary or secondary iodide of one to five carbon atoms, especially methyl iodide. Suitable alkyl iodides include methyl iodide, ethyl iodide, propyl iodide, 2-propyl iodide, 2-iodoethanol, 3-iodopropanol, 2-iodobutane, 1-iodobutane, 1-iodo-4-butanol, and 2-iodo-3-butanol. The most preferred iodoalkane is methyl iodide.

The carbonylation step is carried out in the presence of a carbonylation catalyst and either carbon monoxide or a mixture of carbon monoxide and hydrogen at temperatures and pressures suitable for the formation of both acyl products and hydrogen iodide. Suitable catalysts include the Group VIII metals and Group VIII metal compounds and complexes. Rhodium and rhodium compounds and complexes are the preferred carbonylation catalysts. The catalytically-effective amount of the carbonylation catalysts is well-known and is described in the literature such as the Falbe and Polichnowski references cited hereinabove.

The temperatures and pressures can be varied considerably depending on a number of factors such as the particular catalyst and concentration thereof employed, the presence of catalyst promoters, the reaction rate desired and the particular combination of pressure and temperature used. Typically the carbonylation step is conducted at pressures in the range of about 100 to about 10,000 psig and at temperature of about 100° to about 250° C. The hydrogen donor can be any compound that generates hydrogen iodide as a co-product in the alkyl iodide carbonylation step. Suitable hydrogen donors include alkanols such as methanol, ethanol, propanol, etc. and, especially, water. In addition to the hydrogen donor, the carbonylation reaction may be carried out in the presence of an inert co-solvent, e.g., N-methylpyrrolidinone and triphenyl phosphine oxide, which is a liquid under the conditions employed. The amount of hydrogen donor employed can vary substantially depending on the catalyst used, the presence of a co-solvent, etc. Normally, the hydrogen donor is present in an amount of at least one mole per mole of alkyl iodide.

The oxidation step is conducted in the presence of an oxidant such as hydrogen peroxide or, preferably, an oxygen-containing gas including air, oxygen-enriched air, pure oxygen, and depleted air. The oxidation can be conducted at temperatures and pressures suitable for the formation of elemental iodine. The temperature and pressure are interdependent and can vary considerably. The temperature can range from 25° to about 200° C. The pressure can range from atmospheric to about 4000 psig.

The carbonylation reaction time is dependent primarily on the catalyst, catalyst concentration and the reaction temperature and pressure employed. Generally, higher temperatures and pressures favor shorter reaction times. The process may be operated either continuously or in a batch mode. For large scale operations, a continuous mode is preferred whereas a batch mode may be preferable for small scale operations.

A preferred embodiment of our invention provides for the conversion of methyl iodide to acetic acid and elemental iodine in a continuous (including semicontinuous) manner wherein (1) contacting in a carbonylation zone a mixture of methyl iodide and water with carbon monoxide in the presence of a carbonylation catalyst under carbonylation conditions of pressure and temperature;

(2) removing from the carbonylation zone a product mixture comprising acetic acid, hydrogen iodide, water and catalyst;

(3) feeding the product mixture of (2) to a catalyst separation zone to obtain (a) a liquid stream comprising catalyst and a minor amount of the product mixture for recycle to carbonylation zone (1) and (b) a vapor stream comprising acetic acid, hydrogen iodide and water;

(4) feeding the vapor stream of (3) to a distillation zone and recovering (a) an acetic acid-water mixture and (b) a hydrogen iodide-water mixture from the distillation zone; and (5) contacting the hydrogen iodide-water mixture from (4) with oxygen-containing gas in the liquid phase in an oxidation zone from which is obtained (a) a liquid stream comprising a major portion of the water fed and (b) a liquid stream comprising elemental iodine and a minor portion of the water fed.

The reactor of carbonylation zone (1) can be of any design which provides intimate contact between the methyl iodide and carbon monoxide. For example, the reactor may be equipped with means for agitation or it may be of a columnar design wherein the carbon monoxide is fed through a gas sparger at the base of the reactor to provide a highly agitated reaction mixture. The carbonylation temperatures and pressures generally are within the ranges described hereinabove, the preferred ranges being about 500 to 1500 psig and about 150° to 225° C. The catalyst system preferably comprises the rhodium-based catalysts described in the Falbe and Polichnowski references cited hereinabove. Methyl iodide and water, which may include water recycled from oxidation zone (5), typically are fed to the carbonylation reactor in a methyl iodide:water weight ratio of about 7.9:1.0 to 1.0:1.0, preferably about 1.5:1.0 to 3.0:1.0.

The catalyst removal zone typically is a flash pot wherein the pressure of the system is reduced, e.g., to about 15 to 100 psig, and from about 70 to 95 weight percent of the carbonylation product comprising acetic acid, hydrogen iodide and water is vaporized and fed to distillation zone (4). The remainder of the carbonylation product containing the non-volatile catalyst component(s) is removed from zone (3) and recycled to carbonylation zone (1).

Distillation zone (4) comprises a column equipped with column internals (trays or packing) to provide (i) an upper zone rich in acetic acid and water and a lower zone rich in a constant boiling mixture of hydrogen iodide and water, i.e., a hydrogen iodide/water azeotrope boiling at about 127° C. at 1 atmosphere. Typically, the vapor stream from (3) is fed to the middle portion of the distillation column while maintaining a column base temperature of about 120° to 140° C., a column head temperature of about 105° to 130° C. and a pressure of about 0 to 20 psig. The acetic acid/water vapor removed from the upper portion of the distillation column may be subjected to known refining procedures to provide a sales grade product.

Oxidation zone (5) comprises a reactor or series of reactors wherein the hydrogen iodide/water mixture obtained from distillation zone (4) is contacted in the liquid phase with an oxygen-containing gas as described above. The temperature and pressure within zone (5) are maintained at about 115° to 180° C. and about 10 to 1000 psig for the oxidation reactor. The reaction product then can be introduced to a decanter or crystallizer that provides the means to remove iodine from the water-containing, unreacted hydrogen iodide. Alternatively, a mixture of elemental iodine and water is removed from the base of the oxidation reactor and water containing unreacted hydrogen iodide exits the upper portion of the reactor and may be recycled to carbonylation zone (1). Typically, most of the water of the hydrogen iodide/water feed is removed from the upper portion of the reactor. In a preferred embodiment, recovery of elemental iodine is enhanced by providing cooling means within the upper portion and heating means within the lower portion of a combined oxidation reactor.crystallizer.decanter. Thus, in the preferred operation of oxidation zone (5), the temperature of the stream exiting the upper portion is about 10° to 100° C. and that of the stream exiting the lower portion is about 115° to 150° C.

Our novel process is further illustrated by the following examples. In the carbonylation step, methyl iodide, solvent, rhodium catalyst ($RhCl_3.3H_2O$) and lithium iodide promoter are loaded into a 330 ml autoclave constructed of Hastelloy B2 alloy which is designed to operate in a rocking mode. The autoclave is pressurized twice to 200 psig with a mixture of 95 percent carbon monoxide and 5 percent hydrogen at room temperature and then the gas is vented to purge the autoclave. The autoclave is sealed and pressurized to 200 psig with the 95/5 carbon monoxide/hydrogen mixture and heated and rocked until a temperature of 150° C. is reached, at which time additional carbon monoxidehydrogen mixture is added to increase the autoclave internal pressure to 750 psig. Reactor pressure is maintained by adding 95/5 carbon monoxide/hydrogen at the same rate at which it is consumed by the reactant. When the predetermined time is completed, the autoclave is cooled by a stream of cold air to approximately 25° C. After the gas is vented from the autoclave, the crude product is analyzed by gas chromatography methods.

EXAMPLE 1

Methyl iodide (22.8 g) is carbonylated as described above in the presence rhodium trichloride (0.51 g), lithium iodide (5.04 g) and water (100.0 g) for a period of 2 hours. Gas chromatography analysis of the resulting reaction mixture shows that all of the methyl iodide has been converted primarily to acetic acid and hydrogen iodide.

EXAMPLE 2

Methyl iodide (222.4 g) is carbonylated as described above in the presence rhodium trichloride (0.51 g), lithium iodide (40.4 g) and water (800.0 g) for a period of 4 hours. Gas chromatography analysis shows that all of the methyl iodide has been converted primarily to acetic acid and hydrogen iodide.

EXAMPLE 3

Methyl iodide (23.0 g) is carbonylated as described above in the presence rhodium trichloride (0.50 g), lithium iodide (5.03 g ), water (6.1 g) and N-methylpyrolidinone (102.6 g) for a period of 2 hours. Gas chromatography analysis shows that all of the methyl iodide has been converted primarily to acetic acid and hydrogen iodide.

EXAMPLE 4

Carbonylation reaction mixture (46.81 g) obtain from Example 2 is placed in a 100 mL, heavy walled, glass reactor designed to operate in a shaking mode. The reactor is pressurized twice and vented with 50 psig oxygen. The reactor is sealed, pressurized to 35 psig with oxygen and immersed into a constant temperature bath. After two minutes, additional oxygen is added to increase the reactor internal pressure to 50 psig. The reactor is then heated to and maintained at 100° C. for 2.5 hours with shaking. Reactor pressure is maintained by adding oxygen at the same rate at which it is consumed by the reactants. The oxidation reaction consumed 15.6 millimoles of oxygen. At the end of the 2.5 hour reaction period, the reactor is removed from the constant temperature bath and allowed to cool. Elemental iodine is observed to precipitate from the reaction mixture.

The invention has been described in detail with particular reference to preferred embodiments thereof, but it will be understood that variations and modifications may be effected within the spirit and scope of the invention.

We claim:

1. Process for the continuous conversion of methyl iodide to acetic acid and elemental iodine by the steps comprising:
    (1) contacting in a carbonylation zone a mixture of methyl iodide and water with carbon monoxide in the presence of a carbonylation catalyst under carbonylation conditions of pressure and temperature;
    (2) removing from the carbonylation zone a product mixture comprising acetic acid, hydrogen iodide, water and catalyst;
    (3) feeding the product mixture of (2) to a catalyst separation zone to obtain (a) a liquid stream comprising catalyst and a minor amount of the product mixture for recycle to carbonylation zone (1) and (b) a vapor stream comprising acetic acid, hydrogen iodide and water;
    (4) feeding the vapor stream of (3) to a distillation zone and recovering (a) an acetic acid-water mixture and (b) a hydrogen iodide water mixture from the distillation zone; and
    (5) contacting the hydrogen iodide-water mixture from (4) with oxygen-containing gas in the liquid phase in an oxidation zone from which is obtained (a) a liquid stream comprising a major portion of the water fed and (b) a liquid stream comprising elemental iodine and a minor portion of the water fed.

* * * * *